United States Patent [19]

Luther

[11] Patent Number: 4,747,836
[45] Date of Patent: May 31, 1988

[54] NEEDLE GUARD, AND ASSEMBLY

[75] Inventor: Ronald B. Luther, Newport Beach, Calif.

[73] Assignee: Luther Medical Products, Inc., Santa Ana, Calif.

[21] Appl. No.: 74,693

[22] Filed: Jul. 17, 1987

[51] Int. Cl.$^4$ ............................................. A61M 5/32
[52] U.S. Cl. ..................................... 604/198; 604/263
[58] Field of Search ............... 604/263, 192, 197, 198, 604/164, 171, 162

[56] References Cited

U.S. PATENT DOCUMENTS 4,425,120  1/1984  Sampson et al. .................... 604/198
4,693,708  9/1987  Wanderer et al. .................. 604/198

*Primary Examiner*—John D. Yasko
*Attorney, Agent, or Firm*—Willie Krawitz

[57] ABSTRACT

A needle guard is provided to protect against accidental needle stick injuries following use, and to provide a cover for the needle when shipping.

The needle guard is rotatably mounted at the base of the needle and defines a longitudinal slot which coincides with the needle. When the needle is ready for use, the needle guard is rotated away from the needle; following use, the guard is rotated back to partially enclose the needle. A slotted cylinder is then moved forwardly along the needle guard and is rotated for a short distance to lock and permanently enclose the needle, and particularly the tip portion thereof.

The device may be adapted for use with over-the-needle catheters, and its use facilitates attachment of other devices such as vacutainers to the needle and hub assembly.

6 Claims, 4 Drawing Sheets

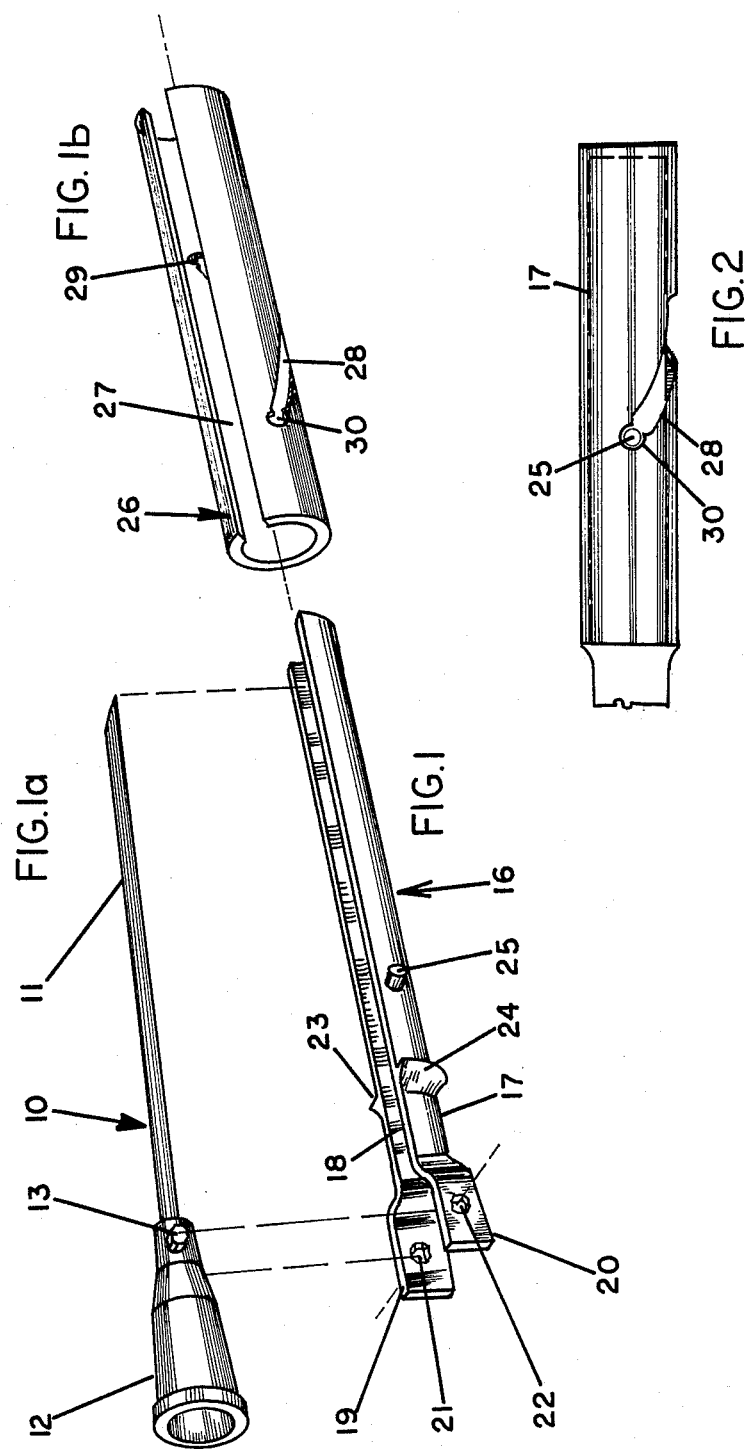

NEEDLE GUARD, AND ASSEMBLY

BACKGROUND OF THE INVENTION

This invention relates to a new and improved needle guard, and the assembly of a guard with a syring needle, I.V. needle, and the like designed to protect against needle stick injuries.

Problems concerning accidental needle sticks are of immediate and increasing concern since they can casue infection such as hepatitis and the AIDS virus.

One type of assembly which provides a needle and guard to prevent these types of injuries is sold by ICU Medical, Inc. However, that particular device requires an extra length of needle and employs a complicated piece of injection molded plastic as the needle guard.

It would be preferred to provide a guard for a needle and assembly thereof, which requires a shorter needle than the ICU device, and having a length which is customarily used for its purpose.

Also, it would be desireable to use fewer and simpler injection molded plastic components for the needle guard. This would of course reduce the cost and enable the device to be handled easier. In addition, if the needle guard could itself be used during operation of the device, this would be an added benefit.

Furthermore, a needle guard, needle and assembly therefor is desired which can be employed with syringes having either a plain tapered or threaded hub; this reduces inventory requirements.

Finally, a locking guard, needle and assembly is desired which provides a double lock effect, which naturally improves the safety features of the device.

THE INVENTION

According to the invention, a locking guard, needle and assembly is provided for a needle comprising a needle guard rotatably mounted at the hub portion of the needle. A longitudinal slit is defined along the guard to enable it to partially enclose the needle during transportation, storage and just prior to use.

A slotted locking ring is rotationally mounted on the locking guard, and subsequent to use, the locking ring is moved forwardly so that the slots engage guide lugs on the locking guard. This enables to ring to rotate around the guide lugs and occlude the needle and tip. The assembly can then be safely discarded.

BRIEF DESCRIPTION OF THE DRAWINGS

FIGS. 1, 1a and 1b are exploded, perspective views of the needle, attached hub, rotatable needle guard and locking ring;

FIG. 2 is an external view in side elevation of the locking ring engaged with the needle guard;

DESCRIPTION OF THE PREFERRED EMBODIMENTS

Figure 3:
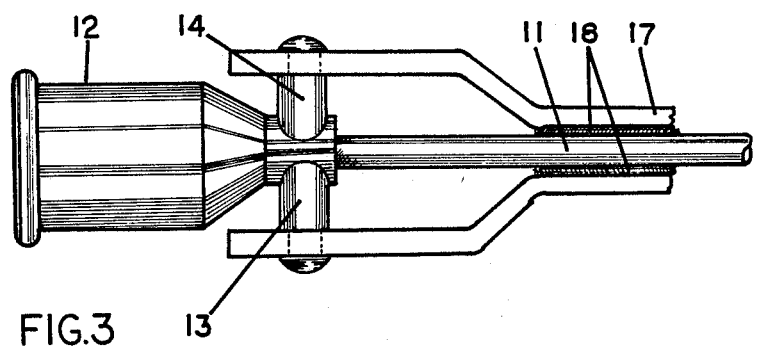
FIG. 3 is an external plan view of the rotatable portion of the needle guard attached to the needle hub.

The needle assembly 10, including a needle guard and closure ring, are shown in an exploded view in FIGS. 1, 1a and 1b. The needle 11 is shown attached to a hub 12 in a conventional manner, and the hub is provided with attached trunnion studs 13, 14. The needle guard portion 16 of the assembly is shown in FIG. 1, and comprises a body length 17 defining a longitudinal slit 18 into which fits the needle. The rotatable end of the needle guard provides trunnion arms 19, 20 defining trunnion bores 21, 22 which are rotatably mounted on the trunnion studs 13, 14. Locking shoulders 23, 24 are defined on the body 17 to provide one mode of engagement for the locking ring, and guide lugs 25, 25 are provided on the body 17 to engage the locking ring and provide another mode of engagement therewith. Both the needle guard and locking ring are constructed of an injection molded plastic such as PVC, polyethylene, polypropylene, nylon, etc., and this of course enables the components to be readily formed. The locking ring 26 is mounted along the needle guard, and defines a slit 27 which coincides with the slit 18 and the needle 11, Locking slots 28, 29 are defined along the locking ring and are adapted to engage the guide lugs 25, 25 when the locking ring is moved forwardly along needle guard. Detents, one detent 30 being shown is provided at the end of each locking slot to ensure engagement with each lug 25, 25 and prevent the locking ring from being loosened out of engagement.

FIG. 2 illustrates the engagement of the locking ring with the needle guard following forward movement along the needle guard and rotational movement around the guide lugs.

Figure 4:
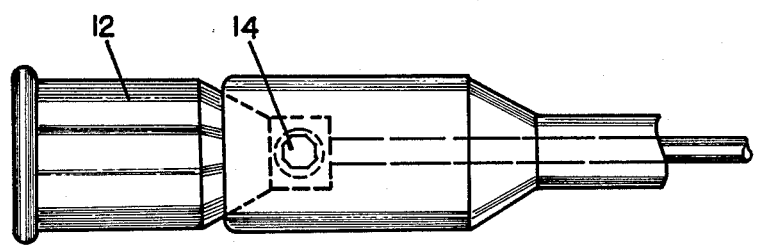
FIG. 4 is an external view in side elevation showing same area as FIG. 3.
Figure 5:
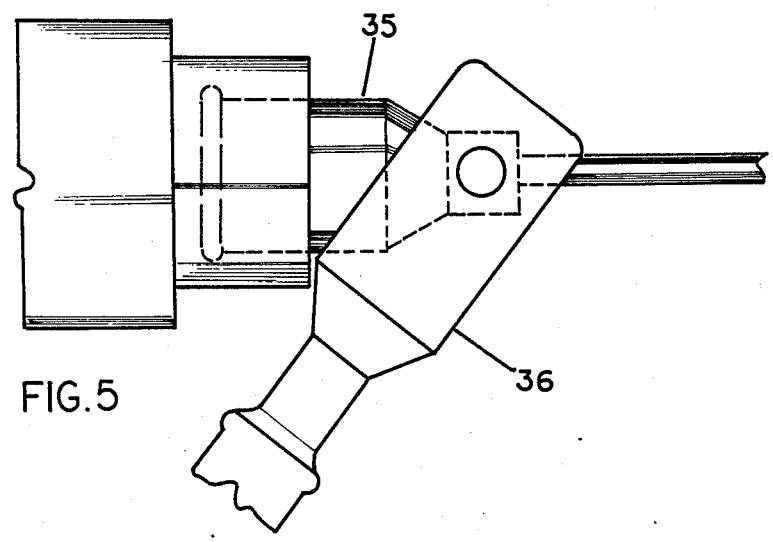
FIG. 5 is an external view in side elevation showing the needle uard rotatably moved out of its protective position from the needle to enable use of the needle.
Figure 10:
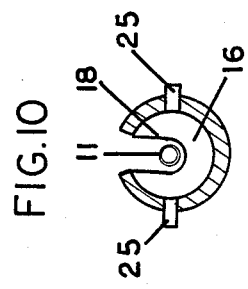
FIG. 10 is a cross sectional view of the device in end elevation showing the needle, needle guard and locking ring when assembled, the locking ring and guard partially enclosing the needle; and, FIG. 11 is a cross sectional view in end elevation of the device following needle use, and after the locking ring has been rotated to protect the needle from a needle stick injury.
Figure 11:
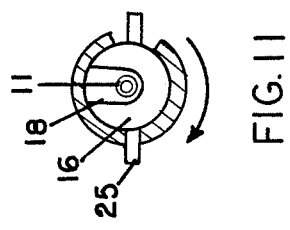

Prior to use, such as during transportation, shipping and storage, the device of this invention is shown assembled in FIGS. 3 and 4, in the closed position. When the device is to be used, the needle guard is moved from its closed position, by rotation, to uncover the needle and hub 35. This is shown in FIG. 5 the needle guard being shown in an open position 36. Following use, the needle guard is then rotated back into position to partly surround the needle 11, and the locking ring is then moved forwardly along the needle guard and rotated around the guide lugs 25, 25 to occlude and protect the used needle. The open and closed positions of the locking ring are further illustrated in FIGS. 10, 11.

It will be appreciated that forward movement of the locking ring 26 along the needle guard 16 will result in the closure ring becoming locked by the locking shoulders 23, 24 of the needle guard. This, of course, will provide another additional means to ensure locking of these two components.

In the retracted position, the needle guard has the capability of functioning as a handle, and this facilitates attachment of devices to the hub such as 'vacutainers', and removal thereof.

Figure 6:
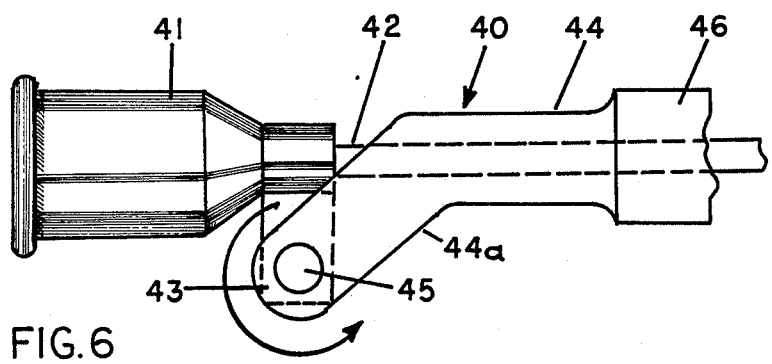
FIGS. 6 and 7 are external views in side elevation showing another embodiment of this invention.
Figure 7:
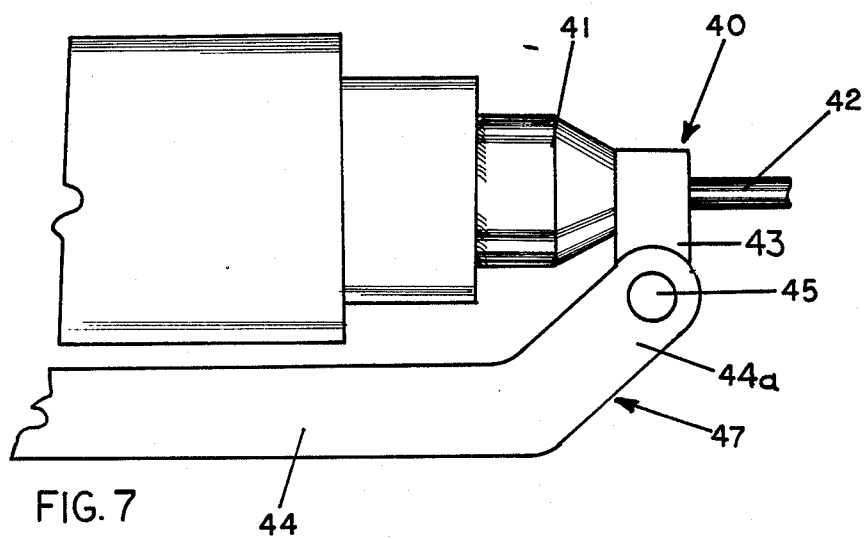
Figure 8:
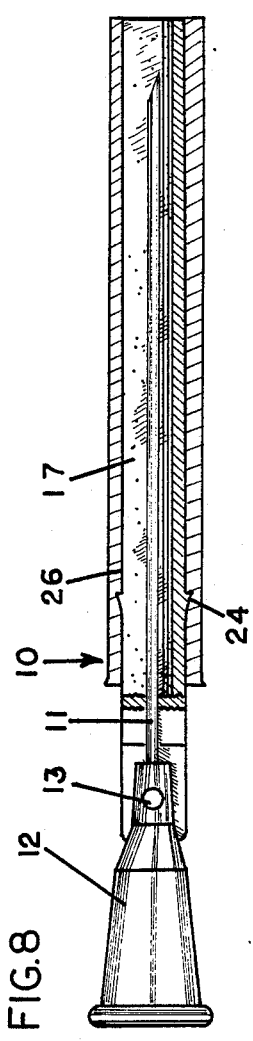
FIG. 8 is a view in sectional side elevation showing the assembled device of FIGS. 1, 1a and 1b.
Figure 9:
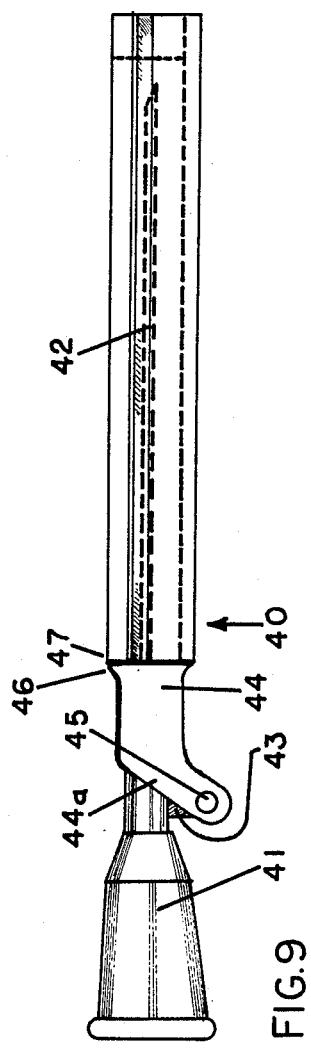
FIG. 9 is an external view in sectional side elevation showing the entire assembled device of the embodiments of FIGS. 6 and 7.

FIGS. 6, 7 and 9 illustrate another embodiment of this invention which enables a greater angle of rotation to be applied to the needle guard. In this embodiment a hub 41 and attached needle 42 are shown protected by a needle cover 40. This includes a guard body 44 which extends into an offset arm 44a which is attached to a depending arm or flange 43 supported by the hub. Trunnion pins, one such pin 45 being shown rotatably mount the needle guard 44 at the offset arm 44a. As in the first embodiment, the function of the locking ring (not shown) is the same, and the locking shoulder 46 on the needle guard shows the approximate location of the locking components.

In FIG. 7, the open position 47 of the needle guard is shown, and it will be noted that this embodiment enables the needle guard to be almost completely out of the user's way, compared to the embodiment of FIG. 1, et seq.

The needle guard and assembly of this invention enables the user to easily manipulate a syringe needle, I.V. needle, and the like, and easily close and lock the device without significant danger. After the device has been used and locked, it becomes virtually tamperproof, except for the deliberate severing of of the components.

I claim:

1. An assembly of a needle guard for a hub and attached needle, comprising:

an elongate guard member mounted on the hub for rotatable movement thereon, the guard member including an elongate, longitudinal slit adapted to interfit with the needle prior to use, the guard member defining engaging means for a rotatable locking member; and, a locking member mounted on the guard member, and adapted for forward movement therealong, the locking member providing an elongate slit coinciding with the slit of the guard member; whereby: i. prior to use the needle is adapted to interfit into the slit of the guard member; ii. during use, the guard member and attached locking member are adapted to rotate away from the needle; iii. following use, the guard member and attached locking member are adapted to rotate back to interfit with the used needle; and, iv. the locking member is adapted to be advanced along the needle guard and rotatably locked along the engaging means while moving the locking slit out of alignment with, and to occlude the needle, thereby protecting against accidental needle stick injuries.

2. The assembly of claim 1, including locking shoulders mounted on the guard member to engage the locking member thereby.

3. The assembly of claim 1, including a flange member depending from the hub, the guard member being mounted rotatably on the flange.

4. The assembly of claim 1, in which the guard member defines trunnion arms mounted on the hub portion of the assembly.

5. The assembly of claim 1, in which the guard member provides locking studs, and the locking member provides at least one locking slit adapted to rotatably engage the locking studs.

6. The assembly of claim 1, in which the guard member and locking member are constructed of an injection molded plastic.

* * * * *